United States Patent [19]
Tanikawa et al.

[11] Patent Number: 4,590,924
[45] Date of Patent: May 27, 1986

[54] ENDOSCOPE SYSTEM

[75] Inventors: Kouji Tanikawa; Koichi Matsui; Akira Taniguchi; Atsushi Amano; Masahide Kanno; Yutaka Takahashi, all of Tokyo, Japan

[73] Assignee: Olympus Optical Co., Ltd., Tokyo, Japan

[21] Appl. No.: 649,527

[22] Filed: Sep. 11, 1984

[30] Foreign Application Priority Data

Sep. 21, 1983 [JP] Japan ................. 58-174709
Oct. 7, 1983 [JP] Japan ................. 58-187958
Oct. 7, 1983 [JP] Japan ................. 58-187959
Oct. 7, 1983 [JP] Japan ................. 58-187960

[51] Int. Cl.$^4$ ............................................. A63B 1/06
[52] U.S. Cl. ......................................... 128/6; 354/62; 358/98
[58] Field of Search ..................... 128/6, 4; 354/62; 358/98

[56] References Cited
U.S. PATENT DOCUMENTS
4,343,300 8/1982 Hattori ................................ 128/6
4,475,540 10/1984 Takamatsu ......................... 128/6

FOREIGN PATENT DOCUMENTS
55-77258 6/1980 Japan .
55-112094 8/1980 Japan .
55-110350 8/1980 Japan .

Primary Examiner—William H. Grieb
Attorney, Agent, or Firm—Frishauf, Holtz, Goodman & Woodward

[57] ABSTRACT

An endoscope system includes an endoscope, an endoscope camera and a light source device. The light source device has an error detection unit for detecting an error of communication data and an error recovery unit for performing an error recovery operation in correspondence with an error content detected by the error detection unit.

14 Claims, 6 Drawing Figures

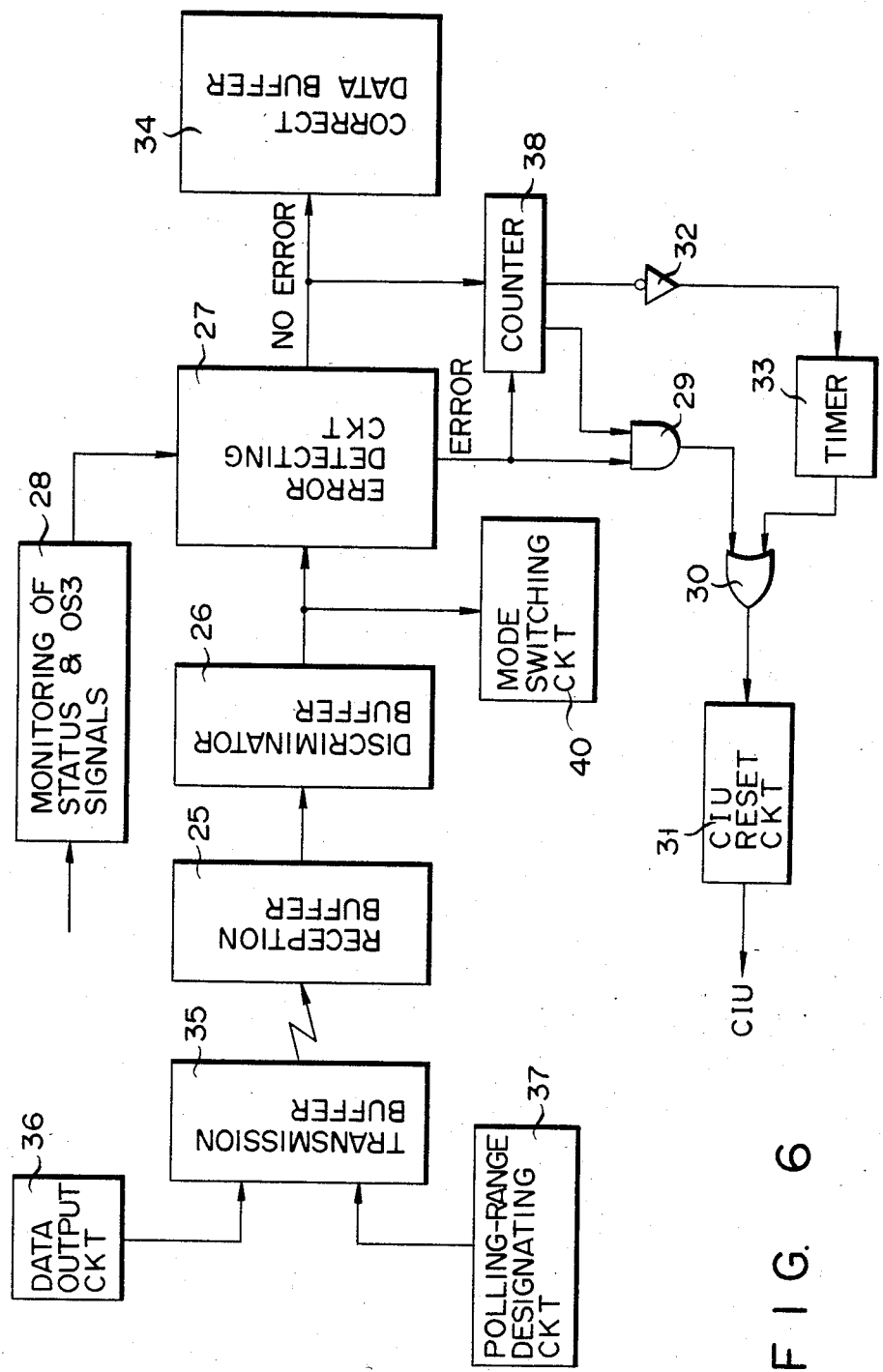
F I G. 6

4,590,924

ENDOSCOPE SYSTEM

BACKGROUND OF THE INVENTION

The present invention relates to an endoscope system and, more paticularly, to an endoscope system having a data communication function.

An endoscope system includes at least an endoscope, an endoscope camera and a light source device. In such an endoscope system, an endoscope, an endoscope camera, and a light source device can have data processing and data communication functions. In data communication, when data is transmitted from a transmission station to a reception station, the reception station generates a response signal when it receives the data. Then, when the transmission station receives this response signal, it can transmit next data. When this response signal is not transmitted from the reception station, the transmission station is set in a data transmission waiting state. On the other hand, the reception station is set in a reception waiting state until it receives all the data to be received. During this data communication, when noise is mixed into the data, a data error occurs, and the correct data communication cannot be performed. Meanwhile, when one of the endoscope, the endoscope camera and the light source device is not of the new type, that is, one of them has no data communication means, the response signal cannot be generated. In this case, a CPU recognizes this as a data error, resulting in a malfunction of the endoscope system.

SUMMARY OF THE INVENTION

It is an object of the present invention to provide an endoscope system having a data communication function which can immediately respond to a data error.

According to the present invention, there is provided an endoscope system comprising an error detecting unit which is provided in an endoscope light source device and detects an error of communication data, an error counter for counting the number of errors which are detected by the error detecting unit, and an error recovering unit for performing an error recovery operation immediately after an error is detected when the number of the errors counted by the error counter is below a predetermined value, and for performing the error recovery operation after a predetermined time period when the number of errors exceeds the predetermined value.

According to the present invention, there is provided an endoscope system comprising, for data communication between an endoscope camera and a light source device, a data transmission unit for transmitting data; and a data reception unit for generating a data reception signal when it receives the data from the data transmission unit; the data transmission unit including a data adding unit for adding predetermined data to normal data in order to release a waiting state of the data reception unit due to a data transmission error.

According to the present invention, there is provided an endoscope system comprising an error detecting unit which is provided in at least one of two communication circuit units provided for an endoscope, an endoscope camera and a light source device and detects a data communication error; and a circuit unit for resetting the other communication circuit unit in response to an error detection by the error detecting unit.

BRIEF DESCRIPTION OF THE DRAWINGS

FIG. 6 is a circuit diagram of an error detection/recovery circuit.

DETAILED DESCRIPTION OF THE PREFERRED EMBODIMENT

Figure 1:
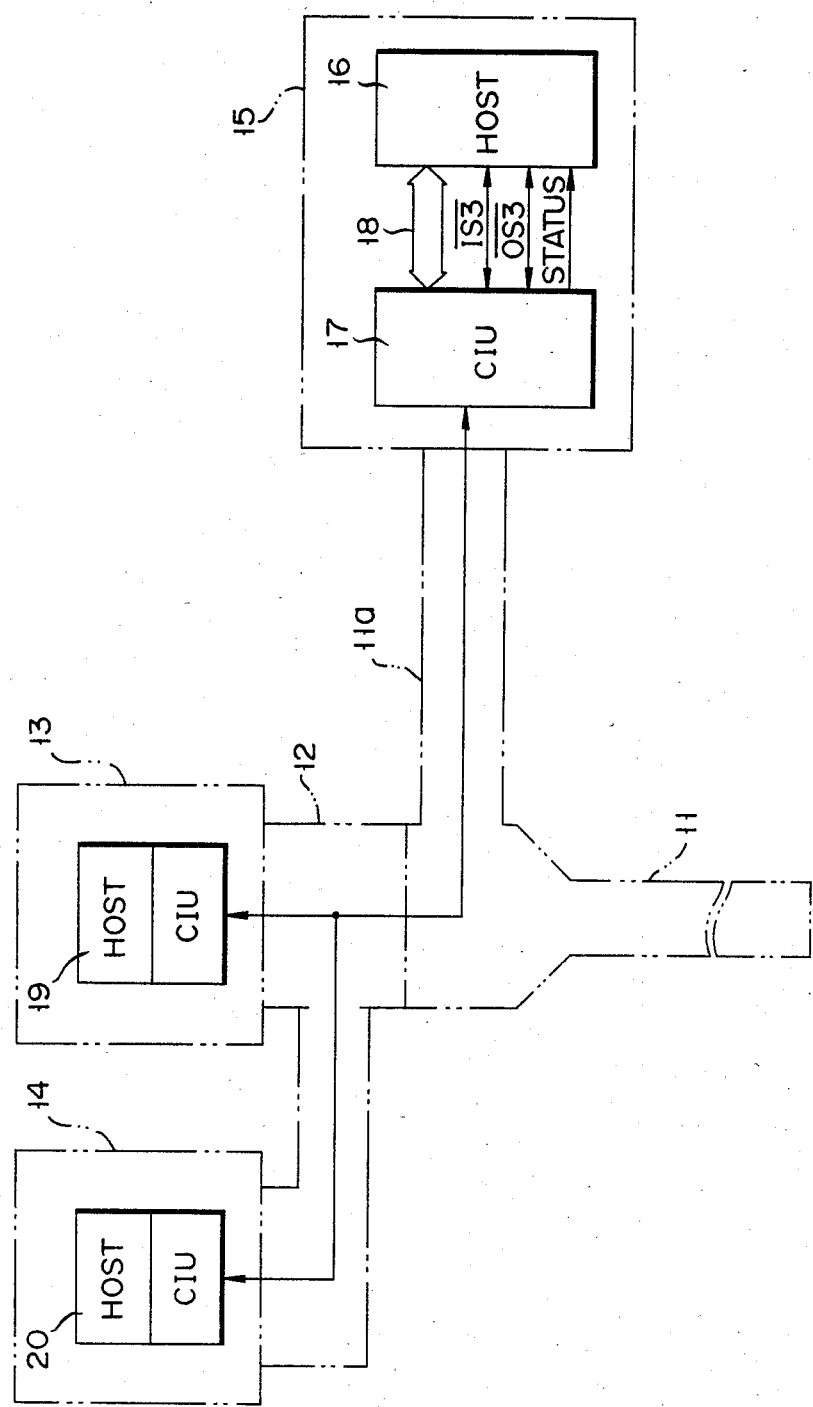
FIG. 1 is a block diagram of an endoscope system according to an embodiment of the present invention.

FIG. 1 shows a block circuit of a communication system of an endoscope system. In FIG. 1, for example, a still camera 13 is mounted on an eyepiece of an endoscope 11 through an adaptor 12. On the other hand, for example, a video camera 14 can be mounted on the adaptor 12. A universal cord 11a of the endoscope 11 is coupled to a light source device 15.

A host computer (HOST) 16 and a communication interface unit (CIU) 17 are respectively provided in the light source device 15. The HOST 16 and the CIU 17 are coupled to each other by a data bus 18 and signal lines $\overline{IS3}$, $\overline{OS3}$ and STATUS. The cameras 13 and 14 respectively comprise circuits 19 and 20 in each of which a HOST and a CIU are mounted in one chip.

Figure 2:
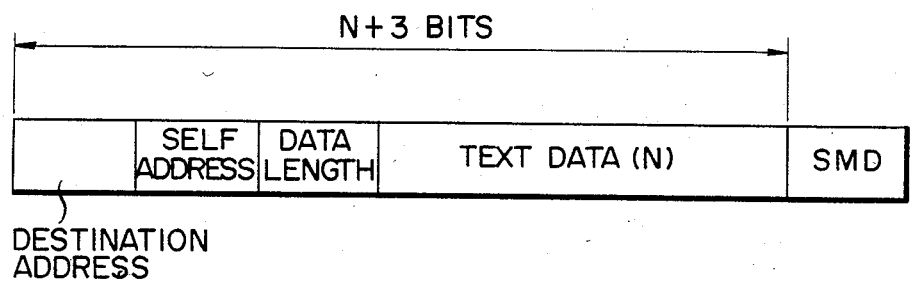
FIG. 2 is a representation showing a data format.

In this endoscope system, communication is performed between the light source device 15 and the cameras 13 and 14. In this case, the light source device 15 becomes a master station, and the cameras 13 and 14 become slave stations. When communication is performed between the HOST 16 and the CIU 17 in the light source device 15, data has a format shown in FIG. 2. According to this data format, the data comprising a destination address, a self address, a data length N and text data have N+3 bytes, and sum check data SMD is added after this data string. The sum check data SMD is a two's complement of a sum (1 byte) obtained by adding N+3 bytes (i.e., from first to last bytes of this data string) by neglecting a carry, that is, data of (N+4)th byte.

Figure 3:
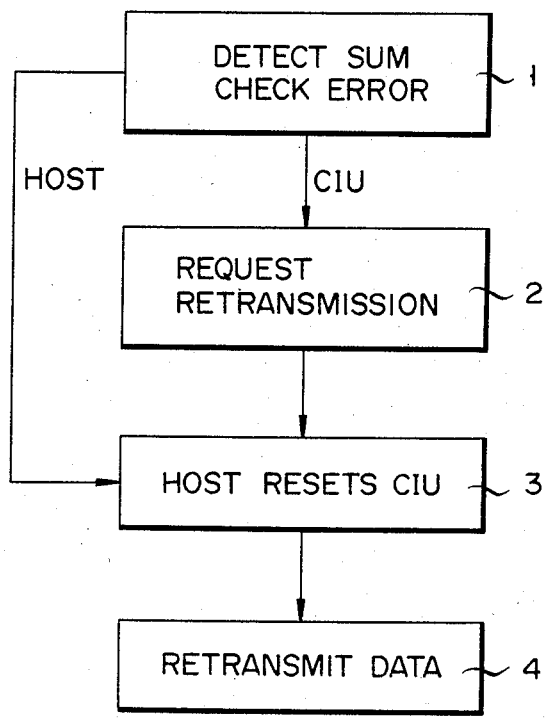
FIG. 3 is a flow chart showing a sequence of the error detection and error recovery operations.

When communication between the HOST 16 and the CIU 17 of the light source device 15 is performed, the sum check operation is also performed. However, in this case, when the CIU 17 detects a sum check error, the error detection and recovery modes are executed in accordance with sequences 1 to 4 in the order named, as shown in the flow chart of FIG. 3. On the contrary, when the HOST 16 detects a sum check error, the error detection and recovery modes are executed in accordance with the order of sequences 1→3→4.

Next, the sum check error detection operation will be described hereinafter. In the sum check error detection operation, the transmission side, for example, the HOST 16 adds N+3 bytes (from first to last bytes of the transmission data), i.e., all bytes of the destination address, the self address, the data length N and the text data in the format of FIG. 2. Then, the two's complement of the sum is added after the text data as the sum check data SMD. On the other hand, the reception side adds all the data string (N+4 bytes) including the data SMD. When the sum becomes 0, it is determined that no error has occurred. When this sum does not become 0, it is determined that an error has occurred. When an error is discriminated in this sum check error detection, the CIU 17 transmits a retransmission request code to the HOST 16. In this case, the CIU 17 transmits the retransmission request code in the following format.

| destination address | self address | data length | 29 | SMD |
|---|---|---|---|---|

In this format, "29" is discriminated as the retransmission request code. When the HOST 16 receives the retransmission request code in accordance with the above format, it resets the CIU 17. When the HOST 16 detects a sum check error, the CIU 17 is immediately reset without transmitting the retransmission request code, and the HOST 16 retransmits the data.

Figure 4:
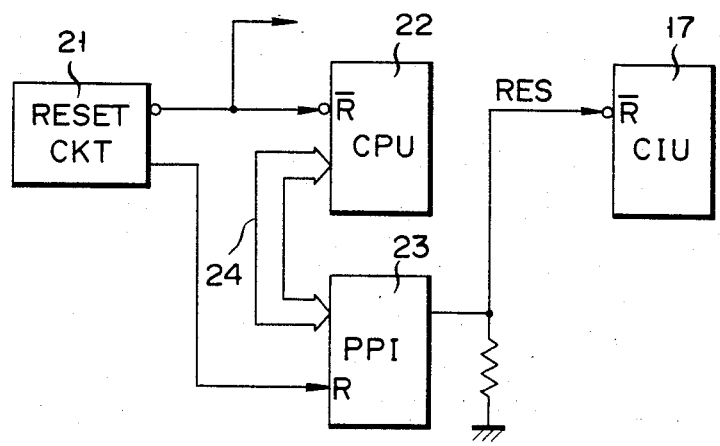
FIG. 4 is a circuit diagram of a circuit for resetting a communication interface unit.

The CIU 17 can be reset in a hardware manner, as shown in FIG. 4. In other words, an output from a reset circuit 21 with respect to the overall system is coupled to reset terminals $\overline{R}$ and R of a central processing unit (CPU) 22 and a parallel port interface (PPI) 23, respectively. The CPU 22 and the PPI 23 are coupled with each other by a data bus 24, and an output RES from the PPI 23 is coupled to a reset terminal $\overline{R}$ of the CIU 17.

In the circuit of FIG. 4, when the CPU 22 is reset by the reset circuit 21, the CPU 22 resets the CIU 17 through the data bus 24 and the PPI 23 during execution of a program. In other words, the CIU 17 is reset by the CPU 22 independent of a reset timing of the reset circuit 21. When an error occurs, the CIU 17 is reset in accordance with execution of the program of the CPU 22.

Figure 5:
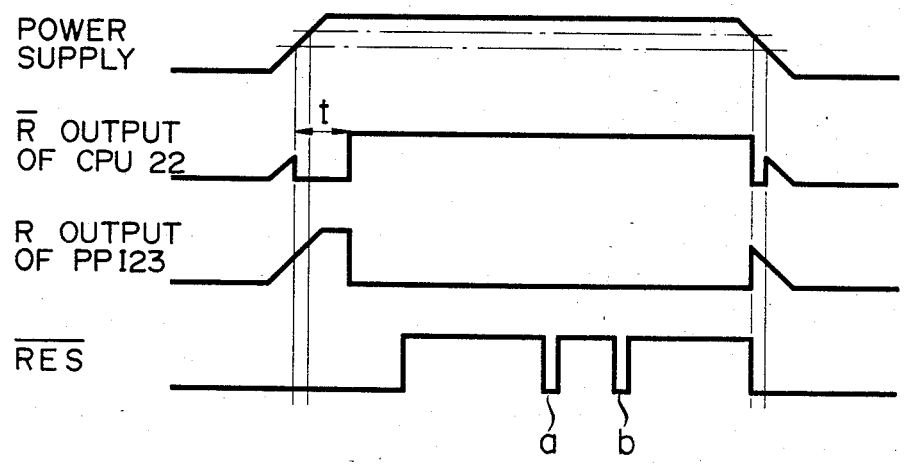
FIG. 5 is a timing chart showing an operation timing of the circuit of FIG. 4.

FIG. 5 shows a timing chart of a reset timing. According to this timing chart, when a power supply is high, the CPU 22 and the PPI 23 are respectively reset and are set at an initial setting interval t of the CPU 22. Note that a and b in the input RES to the CIU 17 represent a state wherein the CIU 17 is arbitrarily reset by the CPU 22.

In FIG. 1, when communication between the HOST 16 and the CIU 17 is performed, it is performed through the data bus 18 (i.e., eight data lines), and the signal lines $\overline{IS3}$, $\overline{OS3}$ and STATUS.

When data is to be transmitted from the CIU 17 to the HOST 16, the CIU 17 sets the line STATUS at low level. In this case, the CIU 17 transmits to the signal line $\overline{OS3}$ a pulse which represents that the data is transmitted. This pulse to the line $\overline{OS3}$ serves as an interrupt signal. When the HOST 16 receives the pulse of the line $\overline{OS3}$, it fetches the data from the CIU 17 and transmits a signal representing data reception to the line $\overline{IS3}$. In the data transmission from the HOST 16 to the CIU 17, the data is transmitted after the HOST 16 recognized that the CIU 17 sets the STATUS at high level. In this case, when the data is set in the HOST 16, a pulse is transmitted to the line $\overline{IS3}$ so as to inform the CIU 17 that data is transmitted. Then, the CIU 17 transmits to the HOST 16 through the line $\overline{OS3}$ a pulse representing that it has received the data. Such data transmission/reception are performed alternately.

When the data is transmitted/received through the data bus as described above, and noise is mixed into the data bus 18, error data are generated, which can be detected by a sum check. However, when excessive data or lack of data due to noise occurs in the data lines $\overline{IS3}$ and $\overline{OS3}$, the number of data which is determined by the data format is undesirably changed. For example, in the case wherein excessive data is received on the data line $\overline{IS3}$, when another pulse is input immediately after receiving the pulse representing that the data has been received, this other pulse is also fetched, that is, the data is fetched twice. In this case, data before the sum check data SMD is processed as the sum check data SMD. Therefore, the sum check error is detected by the sum check operation. However, at the transmission side, one data, i.e., the sum check data SMD still remains. Therefore, the transmission side is set in the state wherein it wants to transmit the data SMD, but cannot transmit, that is, into the waiting state. However, when the data becomes excessive due to noise, the CIU 17 is reset by the sum check error detection, thereby recovering the error data. On the other hand, when lack of data occurs, the reception side is still awaiting data though the transmission side has transmitted all the data. In such a reception waiting state, if additional data is transmitted, the reception of data is completed, thereby releasing the reception waiting state. In this case, the reception data is checked by the sum check operation. Polling address range designation data is used as this additional data having no influence no other data. When respective addresses of the slave stations, for example second to fifth slave stations are designated by the HOST 16, the polling address range designation data means data falling within the range of addresses 2 to 5. In addition, this data has no influence on the data to be generated and transmitted/received in the polling operation.

When the data is transmitted from the HOST 16 to the CIU 17, the line STATUS is kept at high level. When the CIU 17 receives the data, it sequentially polls the slave stations. Then, when the CIU 17 receives a response signal from the slave station, e.g., the camera 14, it sets a new mode, thereby transmitting data to the responded camera 14. During this interval, the line STATUS is kept at low level, and communication from the HOST 16 to the CIU 17 cannot be performed. During this interval, when the CIU 17 polls the slave station, for example, a CIU of the camera 14, if the data is wrong, this polling operation is repeated. In this case, the line STATUS is maintained at low level. The interval in which the line STATUS is maintained at low level is 100 msec in the correct operation mode. Therefore, when the low level interval of the line STATUS is too long, for example, 500 msec, the HOST 16 determines that an abnormality has occurred between the CIU 17 and the CIU of the slave station. Then, the HOST 16 resets the CIU 17, thus avoiding a dead-lock state.

In data communication, when the HOST 16 transmits the data to the CIU 17, the CIU 17 generates a response signal representing that the data has been received. However, in this case, when the response signal is erased by noise, the HOST 16 does not receive this signal. In this case, when the HOST 16 does not receive the response signal within 20 msec of transmitting the data, the HOST 16 determines that an abnormality has occurred in the CIU 17, and resets it.

As described above, when an abnormality occurs, that is, when the reception data is error data, when the line STATUS is kept at low level for 500 msec or more, or when no response signal is transmitted within 20 msec of data transmission, the HOST 16 resets the CIU 17. After resetting, polling range designation is performed. Then, if no response signal is transmitted with respect to this polling range designation, the HOST 16 resets the CIU 17 again. In this manner, the reset operation is repeated until a response signal is transmitted.

When the reset operation is repeated in this manner, it is performed for a short time period, for e.g., the first four times, and thereafter it is performed at an interval of 1 sec. In this manner, an error due to noise generated by sudden thunder, etc., can be recovered at high speed. On the other hand, continuous noise due to the operation of an electric knife or the like can be recovered without influence to an execution speed of other processing.

In the endoscope system (FIG. 1) as described above, assume that an endoscope camera of old type is mounted on the eyepiece of the endoscope 11. When the HOST 16 of the light source device 15 polls this endoscope camera through the CIU 17, no response signal can be generated since this endoscope camera has no communication means. In this case, the HOST 16 determines that the camera is of old type, and it changes from the communication mode to the current mode. Therefore, the endoscope system operates independently of data communication.

FIG. 6 shows hardware of the error detection/recovery circuit. According to FIG. 6, the data is received by a reception buffer 25. The data from the reception buffer 25 is transferred to a discriminator buffer 26. An error detection circuit 27 discriminates whether or not the data has an error. The error detection circuit 27 is coupled to a monitor 28 (e.g., a timer) of the lines STATUS and OS3. When the error detection circuit 27 receives information from this monitor 28, the circuit 27 discriminates whether or not the data has an error by checking a sum of the reception data, an over time, and re-request thereof. Note that when the line STATUS is kept at high level, communication from the HOST 16 to CIU 17 is performed, and when it is kept at low level, that from the CIU 17 to HOST 16 is performed. When the line STATUS is kept at low level for 500 msec or more, it is determined that an error has occurred. If the HOST 16 does not receive a pulse OS3 within 20 msec of transmitting a pulse IS3, it is determined that an error has occurred. It should be noted that pulses IS3 and OS3 here mean "data is transmitted" and "data is received", respectively, and they are exchanged in accordance with a communication direction.

For example, when the data is transmitted from a data output circuit 36 through a transmission buffer 35, a part of the transmission data is erased due to noise and the reception station is set in a reception waiting state. In this state, when next data is transmitted and polling range designation data generated from a polling range designating circuit 37 is received by the CIU 17 before receiving the normal data, the CIU 17 is released from the reception waiting state by this data and performs the sum check operation including this data.

When the error detection circuit 27 detects an error, it supplies a detection signal to a counter 38 and an AND gate 29. The counter 38 counts the number of errors from the detection signal. The counter 38 generates the count signal corresponding to four errors or less to the AND gate 29. The AND gate 29 supplies an error signal of four errors or less to a CIU reset circuit 31, thereby resetting the CIU 17. When the number of errors exceeds four, the output from the counter 38 is supplied to a timer 33 through an inverter 32. The timer 33 is operated in response to the output supplied from the counter 38 through the inverter 32 so as to generate the output signal at intervals of one second. The output signal of the timer 33 repeatedly energizes the CIU reset circuit 31 at intervals of one second through an OR gate 30, thereby repeatedly resetting the CIU 17 at intervals of one second.

Assume that the error detection ciruit 27 detects no error. In other words, when there is no error in the data, correct data is tranferred to a correct data buffer 34. When no error is detected, the counter 38 is reset.

When the discriminator buffer 26 discriminates that a content of the reception buffer 25 is data of the current mode, a mode switching circuit 40 switches the mode to the current mode and the photographic operation mode independent of the data communication is set. The current mode and the new mode are discriminated by the discriminator buffer 26. In the current mode, the photographic operation without accompanying data communication is performed. In the new mode, the photographic operation including data communication between the endoscope camera and the light source device is performed. Therefore, in a combination of an endoscope camera of old type and a light source device of new type, the photographic operation according to the current mode can be performed at a minimum without interfering with the endoscope system.

In the above embodiment, a light source device is described as being of the new type. However, if an endoscope camera is of new type and a light source device is of old type, an endoscope system can be operated in the current mode. When the endoscope system is operated in the new mode and an error occurs, the new mode is switched into the current mode, thereby at least ensuring photographic operation in the current mode. In this case, a mode detection circuit is operated in response to error detection.

What is claimed is:

1. An endoscope system comprising:
an endoscope which is inserted into a body cavity;
an endoscope camera mounted on said endoscope;
a light source device coupled to said endoscope;
data communication means including at least two communication units which are provided respectively in at least two of said endoscope, said endoscope camera and said light source device, one of said units serving as a master station and another of said units serving as a slave station, at least one of said units including means for setting same into a data reception waiting state;
data error detection means for detecting a data error in data communication by said data communication means, said data error including a non-response data error and an abnormal condition data error; and
error recovery means for performing an error recovery operation in response to data error detection by said data error detection means, said error recovery means including means for temporarily releasing a data reception waiting state of said at least one unit of said data communication means due to a data transmission error, thereby preventing said at least one unit from being kept in a data reception waiting state waiting for receipt of data.

2. An endoscope system according to claim 1, wherein said error recovery means comprises error count means for counting the number of errors occurring in data communication of said data communication means and detected by said error detection means; and an error recovery circuit for immediately performing said error recovery operation when the number of errors counted by said error count means is below a predetermined value and for performing said error recovery operation at a predetermined interval when the number of errors counted by said error count means exceeds the predetermined value.

3. An endoscope system according to claim 2, wherein said error recovery circuit comprises a reset circuit for resetting said communication means.

4. An endoscope system according to claim 1, wherein one of said units of said data communication means comprises a data transmission unit for transmitting data; and another of said units of said data communication means comprises a data reception unit for generating a data reception signal upon receiving data from said data transmission unit; and said error recovery means further comprises means for adding predetermined data to normal transmission data in order to release a waiting state of said data reception unit due to a data transmission error.

5. An endoscope system according to claim 1, wherein said error detection means comprises discrimination means for discriminating whether or not communication between said communication units of said at least two of said endoscope, said endoscope camera and said light source device can be performed; and setting means for setting an operation mode without accompanying communication in accordance with a discrimination result of said discrimination means.

6. An endoscope system according to claim 4, wherein said error detection means comprises discrimination means for discriminating whether or not communication between said communication units of said at least two or said endoscope, said endoscope camera of said light source device can be performed; and setting means for setting an operation mode without accompanying communication in accordance with a discrimination result of said discrimination means.

7. An endoscope system according to claim 2, wherein one of said units of said data communication means comprises a data transmission unit for transmitting data; and another of said units of said data communication means comprises a data reception unit for generating a data reception signal upon receiving data from said data transmission unit; and said error recovery means further comprises means for adding predetermined data to normal transmission data in order to release a waiting state of said data reception unit due to a data transmission error.

8. An endoscope system according to claim 7, wherein said error detection means comprises discrimination means for discriminating whether or not communication between said communication units of said at least two of said endoscope, said endoscope camera and said light source device can be performed; and setting means for setting an operation mode without accompanying communication in accordance with a discrimination result of said discrimination means.

9. An endoscope system according to claim 2, wherein said error detection means comprises discrimination means for discriminating whether or not communication between said communication units of said at least two of said endoscope, said endoscope camera and said light source device can be performed; and setting means for setting an operation mode without accompanying communication in accordance with a discrimination result of said discrimination means.

10. An endosscope system comprising:
an endoscope which is inserted into a body cavity;
an endoscope camera mounted on said endoscope;
a light source device coupled to said endoscope;
a data communication means including at least two communication units which are provided respectively in at least two of said endoscope, said endoscope camera and said light source device, one of said units serving as a master station and another of said units serving as a slave station, at least one of said units including means for setting same into a waiting state;
data error detection means for detecting a data error in data communication by said data communication means; and
error recovery means for performing an error recovery operation in response to data error detection by said data error detection means, said error recovery operation including error count means for counting the number of errors occurring in data communication of said data communication means and detected by said error detection means; and an error recovery circuit for immediately performing said error recovery operation when the number of errors counted by said error count means is below a predetermined value and for performing said error recovery operation at a predetermined interval when the number of errors counted by said error count means exceeds the predetermined value.

11. An endoscope system according to claim 10, wherein said error recovery circuit comprises a reset circuit for resetting said communication means.

12. An endoscope system according to claim 10, wherein one of said units of said data communication means comprises a data transmission unit for transmitting data; and another of said units of said data communication means comprises a data reception unit for generating a data reception signal upon receiving data from said data transmission unit; and said error recovery means further comprises means for adding predetermined data to normal transmission data in order to release a waiting state of said data reception unit due to a data transmission error.

13. An endoscope system according to claim 12, wherein said error detection means comprises discrimination means for discriminating whether or not communication between said communication units of said at least two of said endoscope, said endoscope camera and said light source device can be performed; and setting means for setting an operation mode without accompanying communication in accordance with a discrimination result of said discrimination means.

14. An endoscope system according to claim 10, wherein said error detection means comprises discrimination means for discrimination whether or not communication between said communication units of said at least two of said endoscope, said endoscope camera and said light source device can be performed; and setting means for setting an operation mode without accompanying communication in accordance with a discrimination result of said discrimination means.

* * * * *